(12) United States Patent
Sudayama et al.

(10) Patent No.: US 6,403,958 B1
(45) Date of Patent: Jun. 11, 2002

(54) METHOD FOR PREPARING A SAMPLE FOR A TRANSMISSION ELECTRON MICROSCOPE

(75) Inventors: Shoji Sudayama; Takayuki Ishii, both of Chiba (JP)

(73) Assignee: Seiko Instruments Inc. (JP)

( * ) Notice: Subject to any disclaimer, the term of this patent is extended or adjusted under 35 U.S.C. 154(b) by 125 days.

(21) Appl. No.: 09/584,562

(22) Filed: May 31, 2000

(30) Foreign Application Priority Data

Jun. 1, 1999 (JP) .............................. 11-153935

(51) Int. Cl.[7] .................................................. H01J 37/30
(52) U.S. Cl. ........................................ 250/307; 250/309
(58) Field of Search ................................ 250/307, 309, 250/310, 311, 492.21

(56) References Cited

U.S. PATENT DOCUMENTS 5,270,552 A * 12/1993 Ohnishi et al.

* cited by examiner

Primary Examiner—Kiet T. Nguyen
(74) Attorney, Agent, or Firm—Adams & Wilks

(57) ABSTRACT

A sample preparation method is provided where chipping of and damage to a film at an observed location does not occur when cutting with a machining blade is carried out in advance in order to prepare a sample for use with a transmission electronic microscope. The surroundings of an observed location are grooved using a focussed ion beam prior to performing cutting with a machining blade so that the observed location can be isolated from the film composing the sample in a floating island shape. A thin-film for embedding may then be deposited with respect to the grooving, using a focussed ion beam. If necessary, a protective film can also be prepared at the surface of the observed location using a focussed ion beam.

17 Claims, 1 Drawing Sheet

METHOD FOR PREPARING A SAMPLE FOR A TRANSMISSION ELECTRON MICROSCOPE

FIELD OF THE INVENTION

The present invention relates to a method for preparing a sample for a transmission electron microscope employing a focused ion beam apparatus.

DESCRIPTION OF THE RELATED ART

Transmission electron microscope sample preparation methods employing a focused ion beam apparatus are capable of making specified locations of thin-film thinner, and the number of opportunities to use these methods have increased in recent years. In this procedure, a substantial amount of processing is practically impossible using only a focused ion beam. Typically, a large section including an observed location is cut-out from a sample in advance using a machining blade, and is then processed to a thickness of a few tens of micrometers. Thin-film processing is then carried out to reduce the sample to a thin-film of a thickness in the region of 0.1 μm using a focused ion beam.

However, portions of the film at locations other than the location being processed become separated (referred to as "chipping") as a result of a load due to the machining blade when processing employing the aforementioned machining blade is applied to samples containing thin-films. In the worst case, the observation location itself may become chipped, i.e. the film to be observed using a Transmission Electronic Microscope (TEM) may become chipped. Further, because water is employed when cutting with a machining blade, a machining blade cannot be used for cutting when water is not desirable at the observed location.

SUMMARY OF THE INVENTION

The periphery of an observed location is grooved using a focused ion beam to the same thickness as a film thickness for which film chipping is possible or greater prior to cutting with a machining blade so that the observed location is isolated from the film composing the sample.

If necessary, in addition to this grooving, thin-films for embedding or protective use are deposited on a surface of the floating island-shaped observed location using a focused ion beam apparatus. By using this method, the observed location will not be damaged even if film chipping occurs. The observed location is also not influenced by water used during cutting with the machining blade if a surface protection film is provided.

DESCRIPTION OF THE PREFERRED EMBODIMENTS

Figure 1:
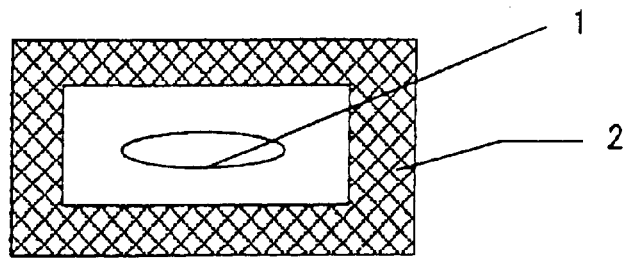
FIG. 1 is a view showing a first embodiment of the present invention.

The following is a description with reference to the drawings of embodiments of this invention. The size, shape and positional relationship of each component of the configurations in the drawings are shown in a manner to provide ease of understanding and are by no means limiting, and conditions placed upon numerical values in the following description are only shown as examples.

First Embodiment

The following is a description with reference to the drawings of a first embodiment of the present invention.

Figure 2:
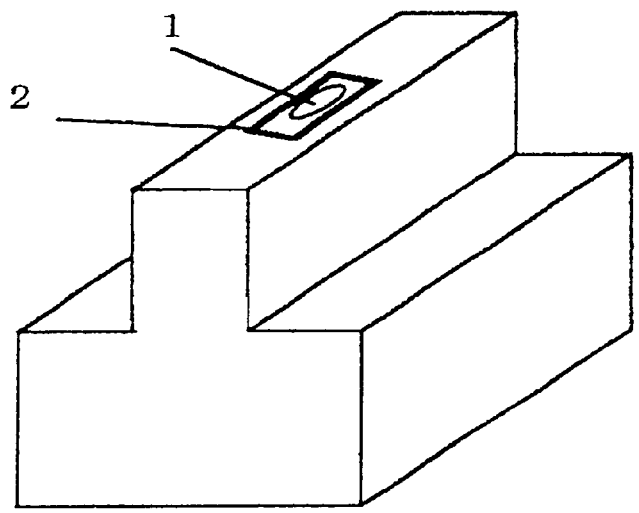
FIG. 2 is a view showing an example of a sample after cutting with a machining blade.

FIG. 1 is a view showing the surface of a sample at a time where a thin-film for embedding is deposited using a focused ion beam at grooving 2, prior to performing cutting with a machining blade and after forming the grooving 2 about the periphery of a sample observing location 1 using a focused ion beam so as to cut out the observed location from a sample-forming film. The thin-film for embedding is deposited as far as the normal sample surface. The reason for providing a thin-film for embedding is as follows. After grooving, sample film of the portion made into an island is connected with a substrate by an area of just a few μm. As a result, chipping may; occur at some time due to the sample film not having good inter-layer film adhesion. The thin-film for embedding is therefore provided to prevent this chipping. It can also be sufficient simply to carve grooves, depending on the sample. FIG. 2 is a view of an example sample after being cut with a machining blade. With this sample, even if chipping occurs at the film during cutting with a machining blade, the chipping of the film will not advance as far as the observed location due to the grooving 2 and thin-film for embedding.

Second Embodiment

Figure 3:
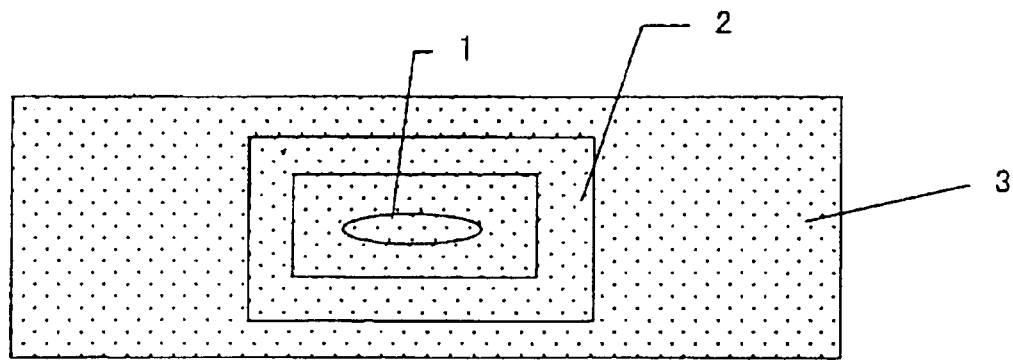
FIG. 3 is a view of where a protective thin-film is provided on the sample surface.

FIG. 3 is a view of a surface of a sample when a protective thin-film 3 is made using a focused ion beam at the observed location surface after completion of the grooving of FIG. 1, and describes a second embodiment. The sample surface will not be influenced by water used while cutting with a machining blade due to the protective thin-film 3 even if the machining blade cutting of FIG. 2 is carried out. The protective thin-film 3 can also be provided after depositing the thin-film for embedding. A material such as tungsten, carbon, or platinum etc. for which FIBCVD (Focused Ion Beam Chemical Vapor Deposition) is possible can be used as the thin-film for embedding or the protective thin-film.

Thin-film processing can then be carried out after the mechanical cutting until the observed location 1 is reached in such a manner that the section becomes of a thickness of approximately 0.1 μm due to the focused ion beam.

According to the invention described in detail above, chipping of and damage to the film at the observed location does not occur when cutting with a machining blade prior to preparing samples for use with transmission electron microscopes employing focused ion beam apparatus.

What is claimed is:

1. A method for preparing a sample for observation by a transmission electron microscope comprising the steps of: forming a groove about the periphery of a location of the sample to be observed using a focused ion beam apparatus so that the location to be observed is isolated from a film composing the sample; and cutting the sample using a machining blade in order to prepare the sample for observation with a transmission electron microscope.

2. A method for preparing a sample for observation by a transmission electron microscope according to claim 1; further comprising the step of depositing a thin-film for embedding or protective use on a surface of the sample at the location to be observed using a focussed ion beam apparatus.

3. A method for preparing a sample for observation by a transmission electron microscope according to claim 1; wherein the step of forming a groove is performed so that a depth of the groove is at least a depth to which chipping of the sample may occur when cutting the sample with the machine blade.

4. A method for preparing a sample for observation by a transmission electron microscope according to claim 1; further comprising the steps of processing the sample to reduce a thickness thereof to about a few tens of $\mu$m and using the focused ion beam apparatus to reduce the thickness to about 0.1 $\mu$m.

5. A method for preparing a sample for observation by a transmission electron microscope according to claim 1; further comprising the steps of processing the sample to reduce a film thickness thereof to about a few tens of $\mu$m and using the focused ion beam apparatus to reduce the film thickness to about 0.1 $\mu$m.

6. A method for preparing a sample for observation by a transmission electron microscope according to claim 1; further comprising the step of depositing a thin film on a surface of the sample at the location to be observed.

7. A method of treating a sample prior to observation with a microscope, comprising the steps of: forming a groove in the sample so that a portion of the sample to be observed by the microscope is disposed at a first side of the groove; and cutting the sample with a machine blade at a second side of the groove opposite the first side to prepare the sample for observation.

8. A method of treating a sample prior to observation with a microscope according to claim 7; wherein the step of forming the groove is performed prior to the step of cutting the sample.

9. A method of treating a sample prior to observation with a microscope according to claim 7; wherein the step of forming a groove is performed so that the groove is a closed pattern enclosing the portion of the sample to be observed.

10. A method of treating a sample prior to observation with a microscope according to claim 7; wherein the step of forming a groove is performed using a focused ion beam apparatus.

11. A method of treating a sample prior to observation with a microscope according to claim 7; further including the step of observing the cut sample with a transmission electron microscope.

12. A method of treating a sample prior to observation with a microscope according to claim 7; further comprising the step of depositing a thin film on a surface of the sample at the portion to be observed.

13. A method of treating a sample prior to observation with a microscope according to claim 12; wherein the step of depositing a thin film is performed using a focussed ion beam apparatus.

14. A method of treating a sample prior to observation with a microscope according to claim 7; wherein the step of forming a groove is performed so that a depth of the groove is at least a depth to which chipping of the sample may occur when cutting the sample.

15. A method of treating a sample prior to observation with a microscope according to claim 7; further comprising the steps of processing the sample to reduce a thickness thereof to about a few tens of $\mu$m and using a focused ion beam apparatus to reduce the thickness to about 0.1 $\mu$m.

16. A method of treating a sample prior to observation with a microscope according to claim 7; further comprising the steps of processing the sample to reduce a film thickness thereof to about a few tens of $\mu$m and using a focused ion beam apparatus to reduce the film thickness to about 0.1 $\mu$m.

17. A method of treating a sample prior to observation with a microscope according to claim 7; further comprising the step of depositing a thin film on a surface of the sample at the portion to be observed.

* * * * *